(12) United States Patent
Soto Del Valle et al.

(10) Patent No.: US 12,137,915 B2
(45) Date of Patent: Nov. 12, 2024

(54) ELONGATING WIRES FOR INHIBITING PREMATURE IMPLANT DETACHMENT

(71) Applicant: DePuy Synthes Products, Inc., RAynham, MA (US)

(72) Inventors: Ariel Soto Del Valle, Miami, FL (US); David Blumenstyk, Miami, FL (US); Daniel Solaun, Miami, FL (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 17/685,454

(22) Filed: Mar. 3, 2022

(65) Prior Publication Data

US 2023/0277186 A1 Sep. 7, 2023

(51) Int. Cl.
*A61B 17/12* (2006.01)
*A61B 34/00* (2016.01)
*A61B 17/00* (2006.01)

(52) U.S. Cl.
CPC ............ *A61B 17/12113* (2013.01); *A61B 17/12145* (2013.01); *A61B 34/71* (2016.02); *A61B 2017/00862* (2013.01); *A61B 2017/12054* (2013.01)

(58) Field of Classification Search
CPC .......... A61B 17/12113; A61B 34/71; A61B 17/12145; A61B 2017/00862; A61B 2017/12054; A61B 17/1214; A61B 2017/00526
See application file for complete search history.

(56) References Cited

U.S. PATENT DOCUMENTS

| | | |
|---|---|---|
| 2,220,203 A | 2/1939 | Branin |
| 3,429,408 A | 2/1969 | Maker et al. |
| 4,858,810 A | 8/1989 | Intlekofer et al. |
| 5,108,407 A | 4/1992 | Geremia et al. |
| 5,122,136 A | 6/1992 | Guglielmi et al. |
| D329,698 S | 9/1992 | Loney et al. |
| 5,234,437 A | 8/1993 | Sepetka |
| 5,250,071 A | 10/1993 | Palermo |
| 5,263,964 A | 11/1993 | Purdy |

(Continued)

FOREIGN PATENT DOCUMENTS

| | | |
|---|---|---|
| CN | 104203341 A | 12/2014 |
| CN | 106456422 A | 2/2017 |

(Continued)

*Primary Examiner* — Richard G Louis
(74) *Attorney, Agent, or Firm* — Troutman Pepper Hamilton Sanders LLP (57) ABSTRACT

Various systems and methods of deploying an implant to a target location of a body vessel are disclosed. A delivery system can include a tubular body having a lumen extending therethrough. A pull wire can extend through the lumen with the pull wire including a distal portion. An elastic loop wire can include a loop opening which is positioned approximate a distal end of the tubular body and can include a proximal attachment point that is affixed to the pull wire. The elastic loop wire and the pull wire can be positioned to secure the implantable medical device to the delivery system. The elastic loop wire can be effective to inhibit premature detachment of the implantable medical device from the delivery system by inhibiting proximal translation of the pull wire with respect to the loop opening of the elastic loop wire.

20 Claims, 5 Drawing Sheets

(56) References Cited

U.S. PATENT DOCUMENTS

| | | |
|---|---|---|
| 5,334,210 A | 8/1994 | Gianturco |
| 5,350,397 A | 9/1994 | Palermo et al. |
| 5,382,259 A | 1/1995 | Phelps et al. |
| 5,392,791 A | 2/1995 | Nyman |
| 5,484,409 A | 1/1996 | Atkinson et al. |
| 5,536,248 A | 7/1996 | Weaver et al. |
| 5,569,221 A | 10/1996 | Houser et al. |
| 5,899,935 A | 5/1999 | Ding |
| 5,925,059 A | 7/1999 | Palermo et al. |
| 6,113,622 A | 9/2000 | Hieshima |
| 6,203,547 B1 | 3/2001 | Nguyen et al. |
| 6,391,037 B1 | 5/2002 | Greenhalgh |
| 6,454,780 B1 | 9/2002 | Wallace |
| 6,506,204 B2 | 1/2003 | Mazzocchi |
| 6,561,988 B1 | 5/2003 | Turturro et al. |
| 7,367,987 B2 | 5/2008 | Balgobin et al. |
| 7,371,251 B2 | 5/2008 | Mitelberg et al. |
| 7,371,252 B2 | 5/2008 | Balgobin et al. |
| 7,377,932 B2 | 5/2008 | Mitelberg et al. |
| 7,384,407 B2 | 6/2008 | Rodriguez et al. |
| 7,708,754 B2 | 5/2010 | Balgobin et al. |
| 7,708,755 B2 | 5/2010 | Davis, III et al. |
| 7,799,052 B2 | 9/2010 | Balgobin et al. |
| 7,811,305 B2 | 10/2010 | Balgobin et al. |
| 7,819,891 B2 | 10/2010 | Balgobin et al. |
| 7,819,892 B2 | 10/2010 | Balgobin et al. |
| 7,901,444 B2 | 3/2011 | Slazas |
| 7,985,238 B2 | 7/2011 | Balgobin et al. |
| 8,062,325 B2 | 11/2011 | Mitelberg et al. |
| 8,333,796 B2 | 12/2012 | Tompkins et al. |
| 8,926,650 B2 * | 1/2015 | Que ................ A61B 17/12113 606/200 |
| 8,956,381 B2 * | 2/2015 | Que ................ A61B 17/12113 606/200 |
| 9,155,540 B2 | 10/2015 | Lorenzo |
| 9,232,992 B2 | 1/2016 | Heidner |
| 9,314,326 B2 | 4/2016 | Wallace et al. |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,775,706 B2 | 3/2017 | Peterson et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,120 B2 | 5/2017 | Lagodzki et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 9,918,718 B2 | 3/2018 | Lorenzo |
| 10,149,676 B2 | 12/2018 | Mirigian et al. |
| 10,285,710 B2 | 5/2019 | Lorenzo et al. |
| 10,292,851 B2 | 5/2019 | Gorochow |
| 10,420,563 B2 | 9/2019 | Hebert et al. |
| 10,517,604 B2 | 12/2019 | Bowman et al. |
| 10,668,258 B1 | 6/2020 | Calhoun et al. |
| 10,806,402 B2 | 10/2020 | Cadieu et al. |
| 10,806,461 B2 | 10/2020 | Lorenzo |
| 11,951,026 B2 | 4/2024 | Clinger et al. |
| 2001/0049519 A1 | 12/2001 | Holman et al. |
| 2002/0072705 A1 | 6/2002 | Vrba et al. |
| 2002/0165569 A1 | 11/2002 | Ramzipoor et al. |
| 2003/0009208 A1 | 1/2003 | Snyder et al. |
| 2003/0093094 A1 | 5/2003 | Diaz et al. |
| 2003/0181942 A1 | 9/2003 | Sutton et al. |
| 2004/0034363 A1 | 2/2004 | Wilson et al. |
| 2004/0059367 A1 | 3/2004 | Davis et al. |
| 2004/0087964 A1 | 5/2004 | Diaz et al. |
| 2006/0025801 A1 | 2/2006 | Lulo et al. |
| 2006/0064151 A1 | 3/2006 | Guterman |
| 2006/0100687 A1 | 5/2006 | Fahey et al. |
| 2006/0116711 A1 | 6/2006 | Elliott et al. |
| 2006/0116714 A1 | 6/2006 | Sepetka et al. |
| 2006/0135986 A1 | 6/2006 | Wallace et al. |
| 2006/0206139 A1 | 9/2006 | Tekulve |
| 2006/0241685 A1 | 10/2006 | Wilson et al. |
| 2006/0247677 A1 | 11/2006 | Cheng et al. |
| 2006/0276824 A1 | 12/2006 | Mitelberg et al. |
| 2006/0276825 A1 | 12/2006 | Mitelberg et al. |
| 2006/0276826 A1 * | 12/2006 | Mitelberg .......... A61B 17/1215 606/200 |
| 2006/0276827 A1 * | 12/2006 | Mitelberg ........ A61B 17/12022 606/200 |
| 2006/0276830 A1 | 12/2006 | Balgobin et al. |
| 2006/0276833 A1 | 12/2006 | Balgobin et al. |
| 2007/0010850 A1 | 1/2007 | Balgobin et al. |
| 2007/0055302 A1 | 3/2007 | Henry et al. |
| 2007/0083132 A1 | 4/2007 | Sharrow |
| 2007/0203519 A1 | 8/2007 | Lorenzo et al. |
| 2007/0233168 A1 | 10/2007 | Davis et al. |
| 2007/0270903 A1 | 11/2007 | Davis, III et al. |
| 2008/0027561 A1 | 1/2008 | Mitelberg et al. |
| 2008/0045997 A1 | 2/2008 | Balgobin et al. |
| 2008/0097462 A1 | 4/2008 | Mitelberg et al. |
| 2008/0119887 A1 | 5/2008 | Que et al. |
| 2008/0269719 A1 | 10/2008 | Balgobin et al. |
| 2008/0269721 A1 | 10/2008 | Balgobin et al. |
| 2008/0281350 A1 | 11/2008 | Sepetka |
| 2008/0300616 A1 | 12/2008 | Que et al. |
| 2008/0306503 A1 | 12/2008 | Que et al. |
| 2009/0062726 A1 | 3/2009 | Ford et al. |
| 2009/0099592 A1 | 4/2009 | Buiser et al. |
| 2009/0270877 A1 | 10/2009 | Johnson et al. |
| 2009/0312748 A1 | 12/2009 | Johnson et al. |
| 2010/0094395 A1 | 4/2010 | Kellett |
| 2010/0114017 A1 | 5/2010 | Lenker et al. |
| 2010/0206453 A1 | 8/2010 | Leeflang et al. |
| 2010/0324649 A1 | 12/2010 | Mattsson |
| 2011/0092997 A1 | 4/2011 | Kang |
| 2011/0118776 A1 | 5/2011 | Chen et al. |
| 2011/0202085 A1 | 8/2011 | Loganathan et al. |
| 2011/0295303 A1 | 12/2011 | Freudenthal |

(56) References Cited

U.S. PATENT DOCUMENTS

| | | |
|---|---|---|
| 2012/0035707 A1 | 2/2012 | Mitelberg et al. |
| 2012/0041472 A1 | 2/2012 | Tan et al. |
| 2012/0083868 A1 | 4/2012 | Shrivastava et al. |
| 2012/0172913 A1 | 7/2012 | Kurrus et al. |
| 2012/0172921 A1 | 7/2012 | Yamanaka et al. |
| 2012/0179194 A1 | 7/2012 | Wilson et al. |
| 2012/0283768 A1 | 11/2012 | Cox et al. |
| 2012/0289772 A1 | 11/2012 | O'Connell et al. |
| 2013/0066413 A1 | 3/2013 | Jin et al. |
| 2013/0296915 A1 | 11/2013 | Bodewadt |
| 2013/0325054 A1 | 12/2013 | Watson |
| 2013/0338678 A1 | 12/2013 | Loushin et al. |
| 2014/0058435 A1 | 2/2014 | Jones et al. |
| 2014/0135812 A1 | 5/2014 | Divino et al. |
| 2014/0200607 A1 | 7/2014 | Sepetka et al. |
| 2014/0207175 A1 | 7/2014 | Aggerholm |
| 2014/0243883 A1 | 8/2014 | Tsukashima et al. |
| 2014/0277084 A1 | 9/2014 | Mirigian et al. |
| 2014/0277085 A1 | 9/2014 | Mirigian et al. |
| 2014/0277092 A1 | 9/2014 | Teoh et al. |
| 2014/0277093 A1 | 9/2014 | Guo et al. |
| 2014/0277100 A1 | 9/2014 | Kang |
| 2015/0005808 A1 | 1/2015 | Chouinard et al. |
| 2015/0025562 A1 | 1/2015 | Dinh et al. |
| 2015/0119884 A1 | 4/2015 | Fung et al. |
| 2015/0164666 A1 | 6/2015 | Johnson et al. |
| 2015/0182227 A1 | 7/2015 | Le et al. |
| 2015/0230802 A1 | 8/2015 | Lagodzki et al. |
| 2015/0335333 A1 | 11/2015 | Jones et al. |
| 2016/0008003 A1 | 1/2016 | Kleshinski et al. |
| 2016/0022275 A1 | 1/2016 | Garza |
| 2016/0022445 A1 | 1/2016 | Ruvalcaba et al. |
| 2016/0045347 A1 | 2/2016 | Smouse et al. |
| 2016/0157869 A1 | 6/2016 | Elgård et al. |
| 2016/0228125 A1 | 8/2016 | Pederson, Jr. et al. |
| 2016/0278782 A1 | 9/2016 | Anderson et al. |
| 2016/0310304 A1 | 10/2016 | Mialhe |
| 2016/0331383 A1 | 11/2016 | Hebert et al. |
| 2016/0346508 A1 | 12/2016 | Williams et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095258 A1 | 4/2017 | Tassoni et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0105739 A1 | 4/2017 | Dias et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0245864 A1 | 8/2017 | Franano et al. |
| 2017/0245885 A1 | 8/2017 | Lenker |
| 2017/0252064 A1 | 9/2017 | Staunton |
| 2017/0258476 A1 | 9/2017 | Hayakawa et al. |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2017/0367712 A1 | 12/2017 | Johnson et al. |
| 2018/0028779 A1 | 2/2018 | von Oepen et al. |
| 2018/0036508 A1 | 2/2018 | Ozasa et al. |
| 2018/0078263 A1 | 3/2018 | Stoppenhagen et al. |
| 2018/0228493 A1 | 8/2018 | Aguilar et al. |
| 2018/0250150 A1 | 9/2018 | Majercak et al. |
| 2018/0280267 A1 | 10/2018 | Keren |
| 2018/0289375 A1* | 10/2018 | Hebert ............ A61B 17/12118 |
| 2018/0296222 A1 | 10/2018 | Hebert et al. |
| 2018/0325706 A1 | 11/2018 | Hebert et al. |
| 2019/0142565 A1 | 5/2019 | Follmer et al. |
| 2019/0159784 A1 | 5/2019 | Sananes et al. |
| 2019/0192162 A1 | 6/2019 | Lorenzo et al. |
| 2019/0201688 A1 | 7/2019 | Olson |
| 2019/0231566 A1 | 8/2019 | Tassoni et al. |
| 2019/0255290 A1 | 8/2019 | Snyder et al. |
| 2019/0314033 A1 | 10/2019 | Mirigian et al. |
| 2019/0328398 A1 | 10/2019 | Lorenzo |
| 2020/0078024 A1 | 3/2020 | Tekulve |
| 2020/0138448 A1 | 5/2020 | Dasnurkar et al. |
| 2020/0147347 A1 | 5/2020 | Cottone |
| 2020/0187951 A1 | 6/2020 | Blumenstyk |
| 2020/0229957 A1 | 7/2020 | Bardsley et al. |
| 2020/0397444 A1* | 12/2020 | Montidoro ........ A61M 25/0662 |
| 2021/0001082 A1 | 1/2021 | Lorenzo et al. |
| 2021/0045759 A1 | 2/2021 | Merhi et al. |
| 2021/0085498 A1 | 3/2021 | Nygaard et al. |
| 2021/0100555 A1* | 4/2021 | Lorenzo ............ A61M 25/0662 |
| 2021/0186513 A1 | 6/2021 | Hoshino et al. |
| 2021/0196281 A1 | 7/2021 | Blumenstyk et al. |
| 2021/0213252 A1 | 7/2021 | Lorenzo et al. |
| 2021/0338248 A1 | 11/2021 | Lorenzo et al. |

(56) References Cited

U.S. PATENT DOCUMENTS

2021/0346002 A1 11/2021 Lorenzo et al.
2021/0353299 A1 11/2021 Hamel et al.

FOREIGN PATENT DOCUMENTS

| | | |
|---|---|---|
| EP | 1985244 A2 | 10/2008 |
| EP | 2498691 | 9/2012 |
| EP | 3092956 A1 | 11/2016 |
| EP | 3501427 A1 | 6/2019 |
| EP | 3799803 A1 | 4/2021 |
| EP | 3854321 A1 | 7/2021 |
| EP | 1188414 A1 | 3/2022 |
| EP | 4119065 A1 | 1/2023 |
| JP | 2006-334408 A | 12/2006 |
| JP | 2012-523943 A | 10/2012 |
| JP | 2013-78584 A | 5/2013 |
| JP | 2014-399 A | 1/2014 |
| WO | WO 2007/070793 A2 | 6/2007 |
| WO | 2008064209 A1 | 5/2008 |
| WO | WO 2009/132045 A2 | 10/2009 |
| WO | WO 2012/158152 A1 | 11/2012 |
| WO | WO 2016/014985 A1 | 1/2016 |
| WO | WO 2017/066386 A1 | 4/2017 |
| WO | WO 2018/022186 A1 | 2/2018 |
| WO | WO 2020/148768 A1 | 7/2020 |

\* cited by examiner

ELONGATING WIRES FOR INHIBITING PREMATURE IMPLANT DETACHMENT

FIELD OF INVENTION

The present invention relate to aneurysm treatment devices and more particularly, to improved delivery systems for embolic implants that prevent premature implant deployment.

BACKGROUND

Numerous intravascular implant devices are known in the field. Many are deployed mechanically, via systems that combine one or more catheters and wires for delivery. Examples of implants that can be delivered mechanically include embolic elements, stents, grafts, drug delivery implants, flow diverters, filters, stimulation leads, sensing leads, or other implantable structures delivered through a microcatheter. Some obstetric and gastrointestinal implants may also be implanted via similar systems that combine one or more catheters and wires. Devices that may be released or deployed by mechanical means vary greatly in design but can employ a similar delivery catheter and wire system. Many such catheter-based delivery systems include a wire for retention of the implant in the catheter until the time for release of the device. These systems are then actuated by retracting or pulling the wire relative to the catheter. Such a wire is referred to herein as a "pull wire".

One issue with current catheter-based delivery systems is premature detachment of the implantable device. Premature detachment occurs when the implant is detached from the delivery system before reaching the treatment site. This may occur due to the tortuosity experienced by the delivery system as it passes through the vasculature of the patient, which can cause an increase in friction between the "pull wire" and the delivery system causing the pull wire to move proximally while the delivery system is moving distally.

Accordingly, there is a need for an improved implant delivery system that prevents premature detachment of the implant as it is delivered through tortuous vasculature. This disclosure is directed to this and other considerations.

SUMMARY

Various systems and methods of deploying an implant to a target location of a body vessel are disclosed. A delivery system can include a tubular body having a lumen extending therethrough. A pull wire can extend through the lumen with the pull wire including a distal portion. An elastic loop wire can include a loop opening which is positioned approximate a distal end of the tubular body and can include a proximal attachment point that is affixed to the pull wire. The elastic loop wire and the pull wire can be positioned to secure the implantable medical device to the delivery system. The elastic loop wire can be effective to inhibit premature detachment of the implantable medical device from the delivery system by inhibiting proximal translation of the pull wire with respect to the loop opening of the elastic loop wire.

In one aspect, a delivery system for deploying an implantable medical device to a target location of a body vessel is disclosed. The delivery system can include a tubular body that includes a lumen extending therethrough. The delivery system can include a pull wire extending through the lumen. The pull wire can include a distal portion. The delivery system can include an elastic loop wire that has loop opening at a distal portion of the loop wire that is positioned approximate a distal end of the tubular body. The elastic loop wire can include a proximal attachment point that is affixed to the pull wire. The elastic loop wire and the pull wire can be positioned to secure the implantable medical device to the delivery system. The elastic loop wire can be effective to inhibit premature detachment of the implantable medical device from the delivery system by inhibiting proximal translation of the pull wire with respect to the loop opening of the elastic loop wire.

In some embodiments, the tubular body can include a proximal tube, a support coil distal to the proximal tube, and a distal tube that is distal to the support coil.

In some embodiments, the pull wire is translated proximally by more than approximately 6 millimeters to thereby release the implantable medical device from the delivery system.

In some embodiments, the elastic loop wire is configured to stretch in response to the proximal translation of the pull wire.

In some embodiments, the stretching of the elastic loop wire applies tension to the pull wire that inhibits proximal translation of the pull wire with respect to the loop opening of the elastic loop wire.

In some embodiments, the support coil can include interference cuts.

In some embodiments, the distal tube can further include a compressed distal portion that is positioned approximate the implantable medical device. The compressed distal portion can provide an elastic force against the implantable medical device to thereby facilitate the release of the implantable medical device from the delivery system.

In some embodiments, the compressed distal portion can further include a spiral-cut portion of the distal tube.

In some embodiments, the elastic loop wire has a Young's Modulus of approximately 2 GPa.

In some embodiments, the proximal attachment point of the elastic loop wire can include a weld to the pull wire.

In some embodiments, the proximal attachment point of the elastic loop wire can include one or more knots between respective ends of the loop wire and the pull wire.

In some embodiments, the pull wire is constructed of a nonelastic material.

In some embodiments, the distal tube can further include interference cuts in the tubular body.

In another aspect, a method is disclosed. The method can include providing a sub-assembly. Providing the sub-assembly can include providing an implantable medical device approximate a distal end of a pull wire. Providing the sub-assembly can include positioning an elastic loop wire including a loop opening at a distal portion of the loop wire approximate a locking portion of the implantable medical device. Providing the sub-assembly can include positioning the loop opening through the locking portion of the implantable medical device. Providing the sub-assembly can include positioning the distal end of the pull wire through the loop opening thereby securing the implantable medical device to the sub-assembly. Providing the sub-assembly can include attaching a proximal attachment point of the elastic loop wire to the pull wire. The method can include providing a tubular body comprising a lumen extending therethrough. The method can include positioning the sub-assembly at least partly within the lumen such that the implantable medical device abuts a distal end of the tubular body. The method can include securing a proximal end of the pull wire to a proximal end of the tubular body, thereby securing the implantable medical device to the tubular body.

In some embodiments, the method can include translating the pull wire proximally by more than 6 millimeters to thereby release the implantable medical device from the tubular body.

In some embodiments, the method can include causing the elastic loop wire to stretch in response to proximal translation of the pull by less than approximately 6 millimeters and applying tension to the pull wire by the stretched elastic loop wire to thereby inhibit proximal translation of the pull wire with respect to the loop opening of the elastic loop wire.

In some embodiments, the tubular body can include a proximal tube, a proximal support tube disposed in the lumen of the tubular body, a support coil distal to the proximal tube, and a distal tube distal to the support coil.

In some embodiments, the method can include attaching the proximal attachment point of the elastic loop wire to the pull wire by tying one or more knots between respective ends of the loop wire to the pull wire.

In some embodiments, the distal tube can further include a compressible distal portion and the method can include compressing the compressible distal portion, translating the pull wire proximally by more than approximately 6 millimeters, and decompressing the compressible distal portion to thereby providing an elastic force against the implantable medical device that facilitates the release of the implantable medical device from the tubular body.

In some embodiments, the method can include attaching the proximal attachment point of the elastic loop wire to the pull wire by welding respective ends of the elastic loop wire to the pull wire.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

DETAILED DESCRIPTION

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the pertinent art from the following description, which is by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the pertinent art in view of the teachings herein. Such modifications and variations are intended to be included within the scope of the claims.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

Figure 1:
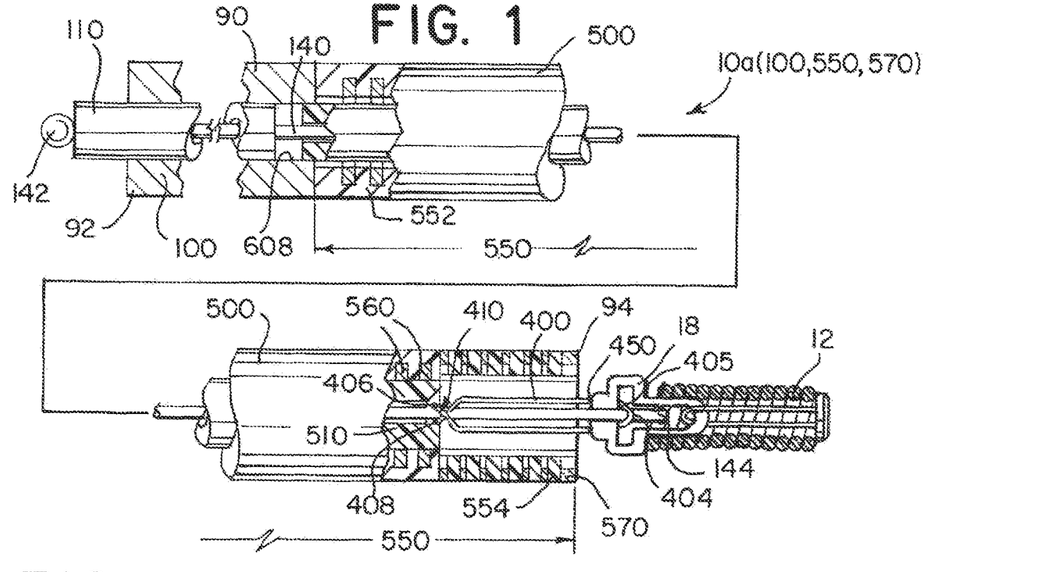
FIG. 1 an illustration of a delivery system and implant, according to aspects of the present invention.

Turning to the figures, FIG. 1 shows an example delivery system 10 for deploying an implantable medical device 12 to a target location of a body vessel. The example delivery system 10 can include a proximal tube 100, a support coil 550 positioned distal to the proximal tube 100, and a distal tube 570 positioned distal to the support coil 550. The proximal tube 100, support coil 550, and distal tube 570 may collectively have a lumen 608 extending therethrough. That is, lumen 608 extends from a proximal end of proximal tube 100, through support coil 550, and through distal tube 570. Collectively, proximal tube 100, support coil 550 and distal tube 570 can be referred to as a tubular body 90. The tubular body can include a proximal end 92 and a distal end 94, as shown in FIG. 1. Implant 12 can be positioned distal to the distal tube 570. Positioned within the lumen 608 of the support coil 550 can be an inner support tube 510. Inner support tube 510 can be welded or otherwise attached to the inner sidewall of support coil 550. Inner support tube 510 can provide structural support to the support coil 550. The support coil 550 can be characterized by interference cuts 560 that can be formed from the sidewall of support coil 550. The interference cuts 560 can provide a high level of flexibility to support coil 550. A sleeve 500 can surround the coiled section. A pull wire 140 can extend through the lumen 608 of delivery system 10. Within lumen 608 of proximal tube 100 can be positioned a proximal support tube 110. Proximal support tube can be welded or otherwise attached to the inner sidewall of proximal tube 100. Both proximal support tube 110 and inner support tube 510 can be considered as part of tubular body 90. Proximal support tube 110 can be considered to be located on proximal end 92 of the tubular body 90. The pull wire 140 can include a pull wire bead 142 located on a proximal end of pull wire 140. The pull wire bead 142 can be sized such that the pull wire bead 142 is larger than the space between the proximal support tube 110 such that the pull wire bead 142 interferes with the proximal support tube 110 and proximal support tube 110 retains the pull wire bead 142 proximal to the proximal tube 100.

A loop wire opening 405 of loop wire 400 can be located at a distal portion 404 of loop wire 400 and can extend through a locking member 18 of implant 12. The distal end 144 of pull wire 140 can be positioned through the loop wire opening 405 of loop wire 400 to secure implant 12 to the delivery system 10. The proximal portion of the loop wire 400 can be attached to the pull wire 140 approximately at the distal end 554 of support coil 550, for example by attaching loop wire proximal ends 406, 408 to the pull wire 140 at a proximal attachment point 410. The attachment method of loop wire 400 to pull wire 140 can be of any type known in the pertinent art, including but not limited to welding proximal ends 406, 408 to pull wire 140 and/or forming knots between proximal ends 406, 408 and the pull wire 140. According to some embodiments, the loop wire 400 can be made of an elastic material, such that proximal translation of the pull wire 140 can cause the loop wire 400 to stretch and become tensioned, which provides a resistant force against further proximal translation of pull wire 140. Accordingly, the elastic loop wire 400 can be effective to prevent premature detachment of implant 12 from delivery system 10. Additionally, the loop wire 400 can be effective to hold distal tube 570 in compression until implant 12 is released from delivery system 10. Collectively, implant 12, elastic loop wire 400, and pull wire 140 can be referred to as a subassembly 450 of the delivery system 10, as can be seen in FIG. 1.

When the delivery system 10 is assembled, the support coil 550 and sleeve 500 can be more flexible than the distal tube 570 and the proximal tube 100. One way to measure flexibility is to perform a three-point bend test wherein a portion of the delivery system 10 is held fixed at two end points, a force is applied perpendicularly to the delivery system 10 centrally between the points, and flexibility is quantified by the length of deflection of the delivery system 10 caused by the force. When measured in this way, in some examples, the support coil 550 and sleeve 500 can be about 1.5 times more flexible than the distal tube 570 and about 20 times more flexible than the proximal tube 100. That is, when the three-point test is performed identically on the three sections 100, 550, and 570, the coiled section deflect over a length that is about 1.5 times the deflection of the distal tube 570 and about 20 times the length of deflection of the proximal tube 100. Flexibility can be measured in other ways as would be appreciated and understood by a person having pertinent skill in the requisite art. When the delivery system 10 is assembled, the support coil 550 and sleeve 500 can be more flexible than the distal tube 570 and the proximal tube 100 as flexibility is determined by other means as would be known to a person of ordinary skill in the art.

According to some embodiments, the distal tube 570 can include a compressible distal portion 300, which can be compressed and formed from a spiral-cut portion of the distal tube 570, formed by a laser cutting operation. Additionally, or alternatively, the compressible distal portion 300 can be formed of a wound wire, spiral ribbon, or other arrangement allowing axial adjustment according to the present invention. Preferably, compressible distal portion 300 is in the elongated condition at rest and automatically or resiliently returns to the elongated condition from a compressed condition, unless otherwise constrained. In some embodiments, the loop wire 400 is effective to hold the compressed distal portion 300 in compression while the implant 12 is delivered to the treatment site.

Pull wire 140 can be constructed out of any suitable material, for example, pull wire 140 can be constructed of stainless steel or memory shape material, such as nitinol. According to some embodiments, pull wire 140 can additionally be coated with polytetrafluoroethylene (PTFE).

Figure 2:
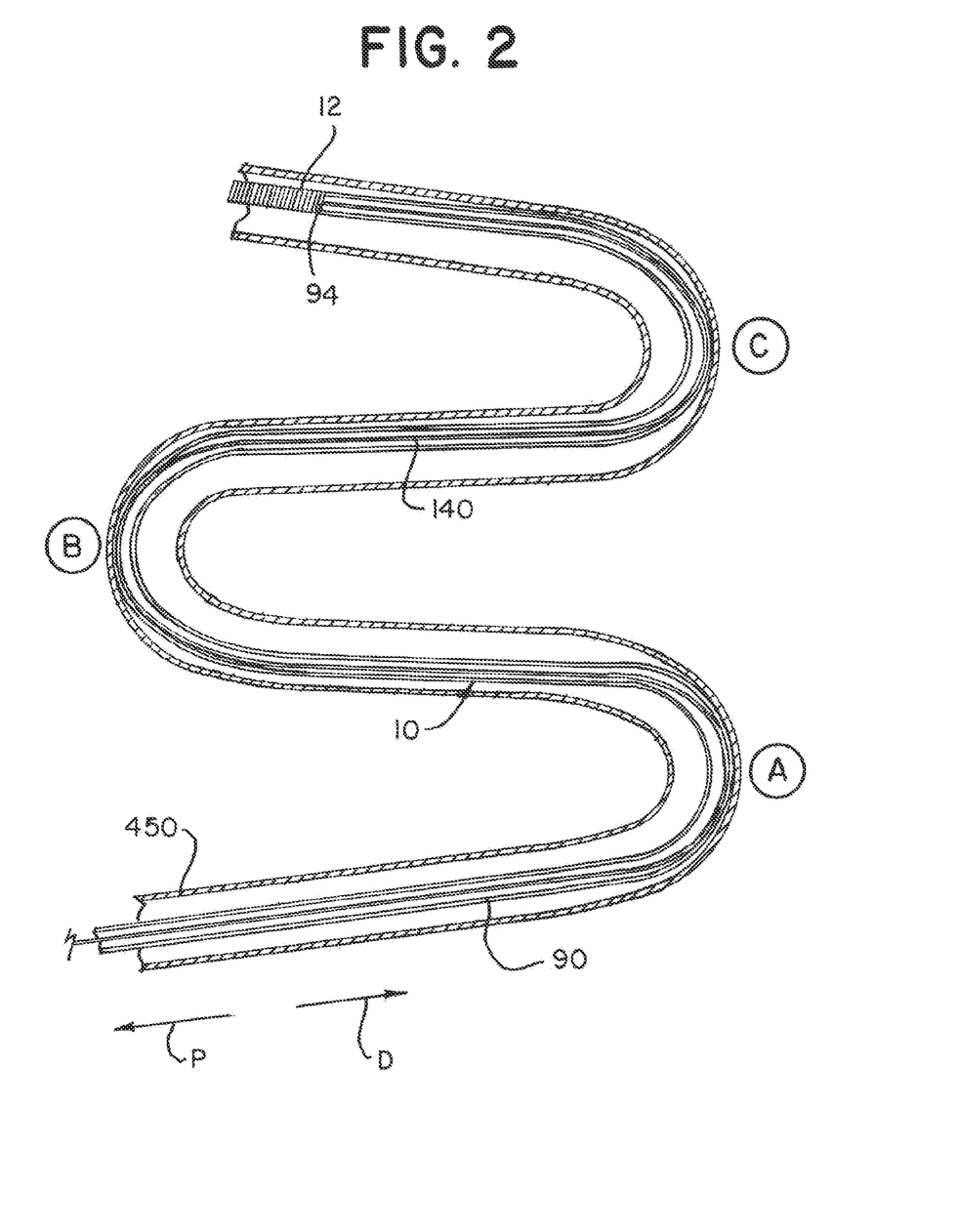
FIG. 2 is an illustration of a delivery system navigating a body lumen according to aspects of the present invention.

FIG. 2 illustrates positioning of an implant 12 such as an embolic coil suitable for aneurysm treatment, a guide catheter 450, and a delivery system 10 including a tubular body 90 and a pull wire 140 within tortuous vasculature (vasculature not illustrated). At bends A, B, and C, the tubular body 90 can extend to a sidewall of the guide catheter 450 on each outer curve of each bend, and likewise, the pull wire 140 can extend to a sidewall of the tubular body 90 on each outer curve of each bend. During a procedure, the tubular body 90 and pull wire 140 can be fed into the guide catheter 450 in the distal direction D, first passing through bend A, then bend B, and then bend C. As the tubular body 90 and pull wire 140 navigate the bends, the pull wire 140 can translate proximally with respect to the tubular body 90. The elastic loop wire ensures that the proximal translation of the pull wire 140 with respect to the tubular body 90 does not prematurely deploy implant 12 before implant 12 is delivered to the treatment site. As the pull wire 140 translates proximally in relation to the tubular body 90, the elastic loop wire 400 stretches and becomes tensioned, preventing the distal end 144 of pull wire 140 from exiting the loop opening 405 of loop wire 400 and prematurely releasing the implant 12.

Figures 3A, 3B, 3C:
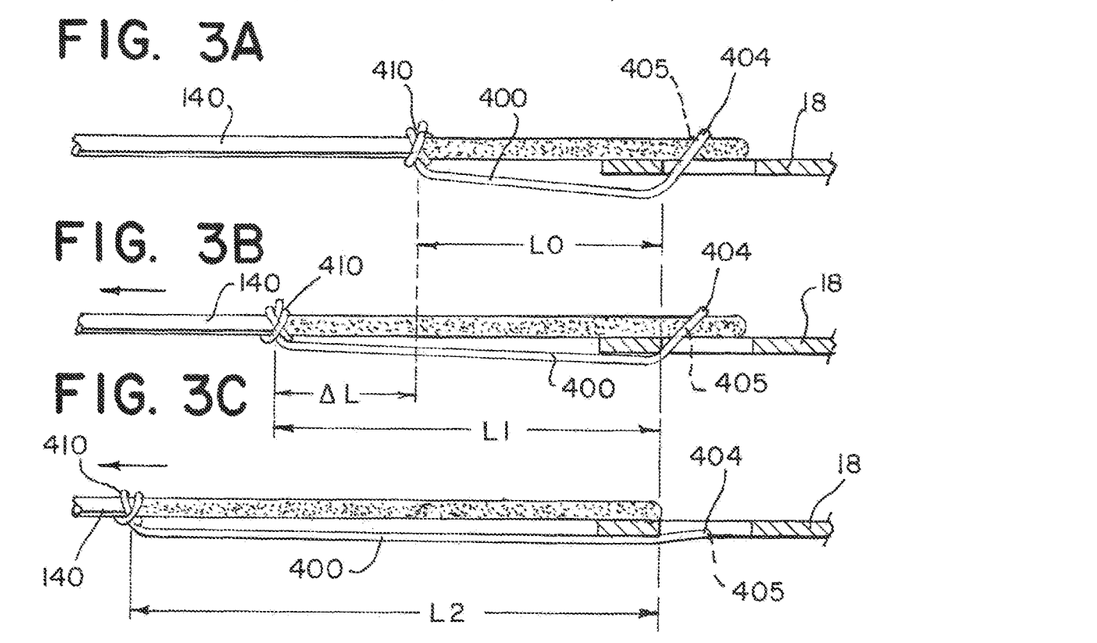
FIGS. 3A-3C illustrates movement of the pull wire and elastic loop wire as the delivery system is delivered through the body lumen of FIG. 2 to a treatment site, according to aspects of the present invention.

FIGS. 3A-3C illustrates the movement of pull wire 140 as the delivery system is delivered through the body lumen of FIG. 2, according to aspects of the present invention. FIG. 3A shows the delivery system 10 as it approaches bend A of FIG. 2. As can be seen, elastic loop wire 400 is in a non-tensioned state with a relaxed length of L0 as measured between where the loop opening 405 of loop wire 400 passes through locking member 18 to the proximal attachment point 410. FIG. 3B shows the configuration of the loop wire 400 and the pull wire 140 as the delivery system 10 rounds bends A, B, and/or C of FIG. 2. As can be seen, while the delivery system 10 is navigating tortuous vasculature of a patient the pull wire 140 can drift proximally with respect to the loop opening 405. The proximal drift of pull wire 140 can cause the loop wire 400 to elongate and become placed into a tensioned state. In an elongated state, the loop wire can have a tensioned length of L1 as measured between where the loop opening 405 of loop wire 400 passes through locking member 18 and the proximal attachment point 410 of loop wire 400. In the state shown in FIG. 3B, the tension in the elastic loop wire 400 is effective to prevent further proximal drift of the pull wire 140 as the delivery system 10 navigates the tortuous vasculature of the patient as the delivery system 10 is delivered to a treatment site. The elastic loop wire 400 can stretch from a non-tensioned length L0 to a tensioned state L1 by elongating a distance ΔL. FIG. 3C shows the elastic loop wire 400 after the delivery system 10 is positioned at the treatment site at the moment a medical professional proximally translates pull wire 140 proximally to release the implant 12 from the delivery system 10. In this configuration, the proximal translation of the pull wire 140 is sufficient to overcome the resistive elastic tension of the tensioned loop wire 400, thereby allowing the distal end 144 of pull wire 140 to exit the loop opening 405 of loop wire 400, which releases the loop opening 405 from tension and allows loop opening 405 to be released from locking member 18 of implant 12, allowing implant 12 to be delivered at the treatment site. As shown, loop wire 400 can have a length L2 between where loop opening 405 passes through locking member 18 and proximal attachment point 410 of loop wire 400 as the implant 12 is released from delivery system 10. Accordingly, in order to release implant 12, the loop wire 400 can be stretched to length L2 that is sufficient to overcome the elastic tension that keeps distal end of pull wire 140 positioned within loop opening 405 of loop wire 400. According to some embodiments, the loop wire 400 can be elongated by more than approximately 6 millimeters in order to release implant 12 from delivery system 10. That is, the difference between non-tensioned loop wire 400 length L0 and released loop wire 400 length L2 can be approximately 6 millimeters according to some embodiments.

Figure 4:
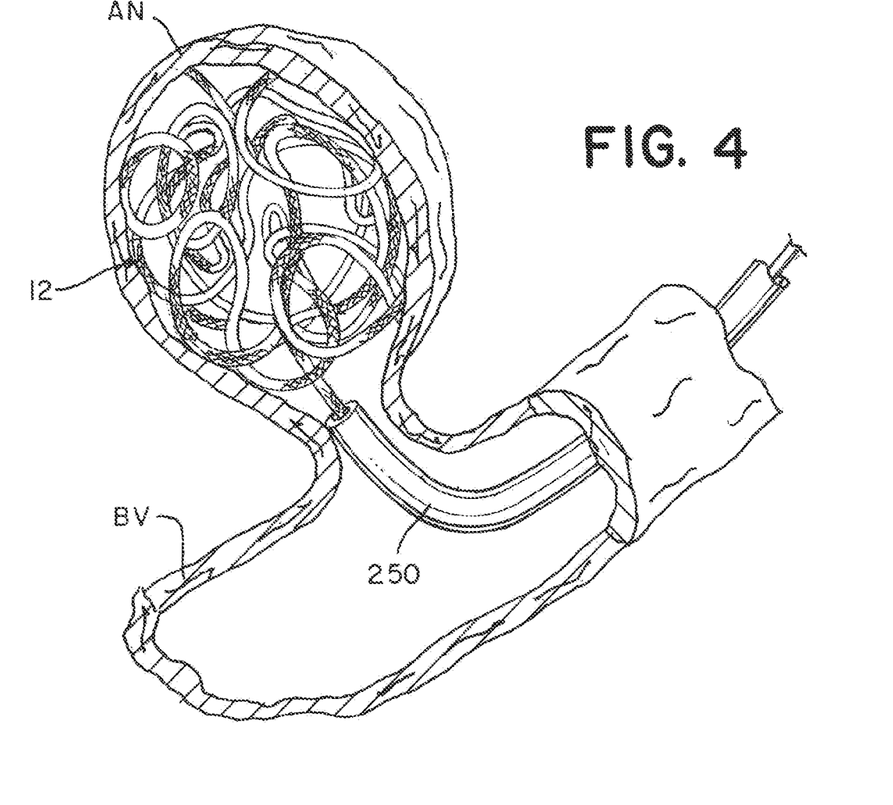
FIG. 4 is an illustration of embolic coils being positioned within an aneurysm according to aspects of the present invention.

FIG. 4 is an illustration of embolic implant 12 being delivered through catheter 250 and positioned within an aneurysm A on a blood vessel BV. The implant can loop and bend with the aneurysm sac to form a thrombotic mass. The implant can loop back on themselves and/or loop next to other implants. As the aneurysm A becomes increasingly packed, overlapping portions of the implant 12 can press into each other.

Figure 5A:
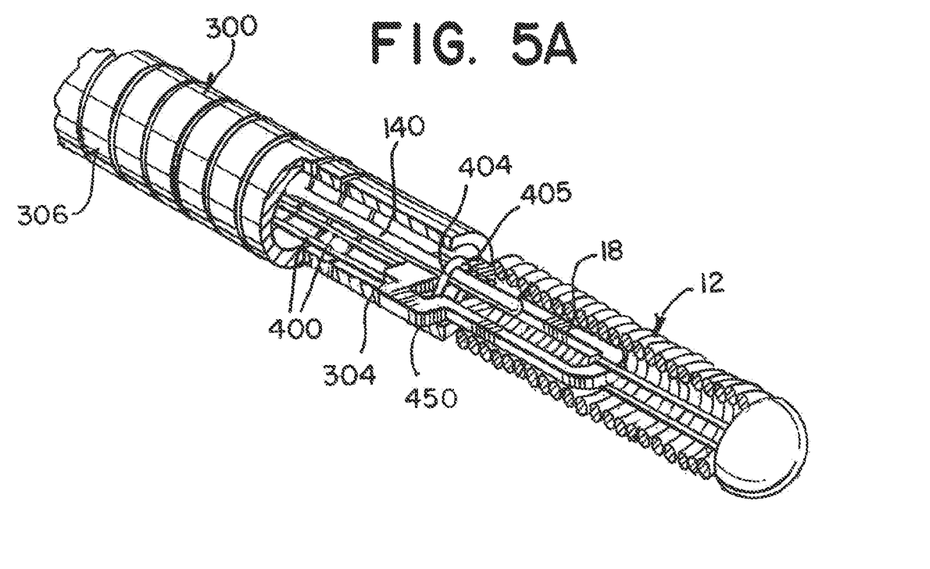
FIGS. 5A-5D illustrate a sequence of steps for releasing an embolic implant from the delivery member, according to aspects of the present invention.
Figures 5B, 5C, 5D:
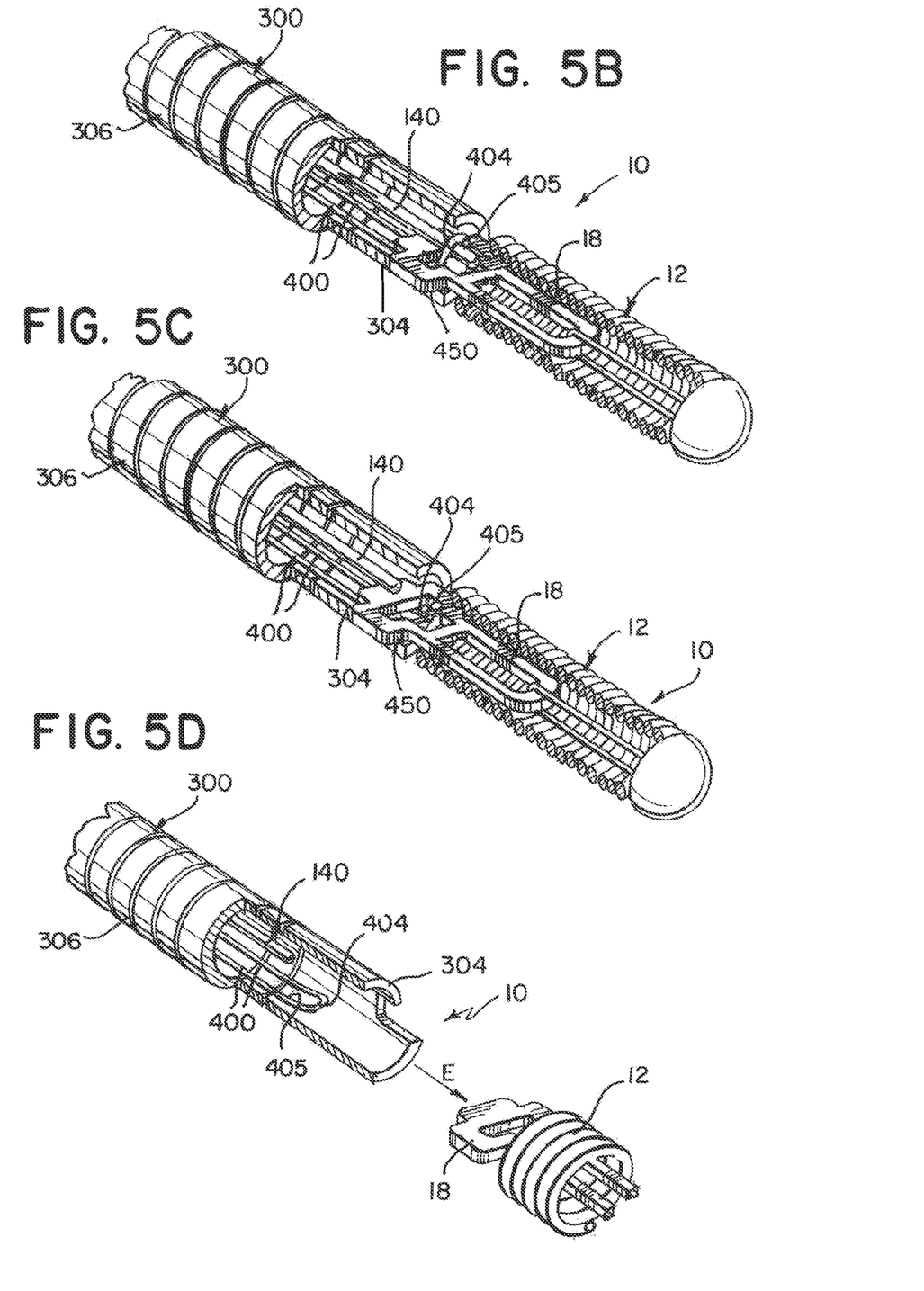

FIGS. 5A-5D illustrate a time sequence of steps for releasing an embolic implant 12 from a delivery system 10. The delivery system 10 can be configured such as illustrated in the previous figures and as otherwise described herein. FIG. 5A illustrates an engagement system including the loop wire 400 and pull wire 140 locked into a locking portion 18 of the medical device 12, thereby forming sub-assembly 450. The spiral cuts 306 of the compressible distal portion 300 can be compressed and the loop wire 400 opening 405 at a distal end 404 of the loop wire 400 can be placed through the locking portion 18. When the pull wire 140 is put through the opening 405 the medical device 12 is now secure. FIG. 5B illustrates the pull wire 140 being drawn proximally to begin the release sequence for the medical device 12. FIG. 5C illustrates the instant the distal end 144 of the pull wire exits the opening 405 and the pull wire 140 is pulled free of the loop wire 400. The distal end 404 of the loop wire 400 falls away and exits the locking portion 18. As can be seen, there is now nothing holding the medical device 12 to the detachment system 10. FIG. 5D illustrates the end of the release sequence. Here, the compressible portion 306 has extended/returned to its original shape and "sprung" forward. An elastic force E is imparted by the distal end 305 of the compressible distal portion 300 to the medical device 12 to "push" it away to ensure a clean separation and delivery of the medical device 12.

The compressible portion 306 can have a difference in length (distance of compression) when measured in the compressed configuration and the original, uncompressed configuration of about 0.5 mm to about 0.75 mm. Greater elastic force E can be achieved by using a greater distance of compression. The distance of compression can be determined by the sizing of the loop wire 400, the shape of the locking portion 18, and the shape of the distal end 304 of the compressible distal portion 300.

Figure 6:
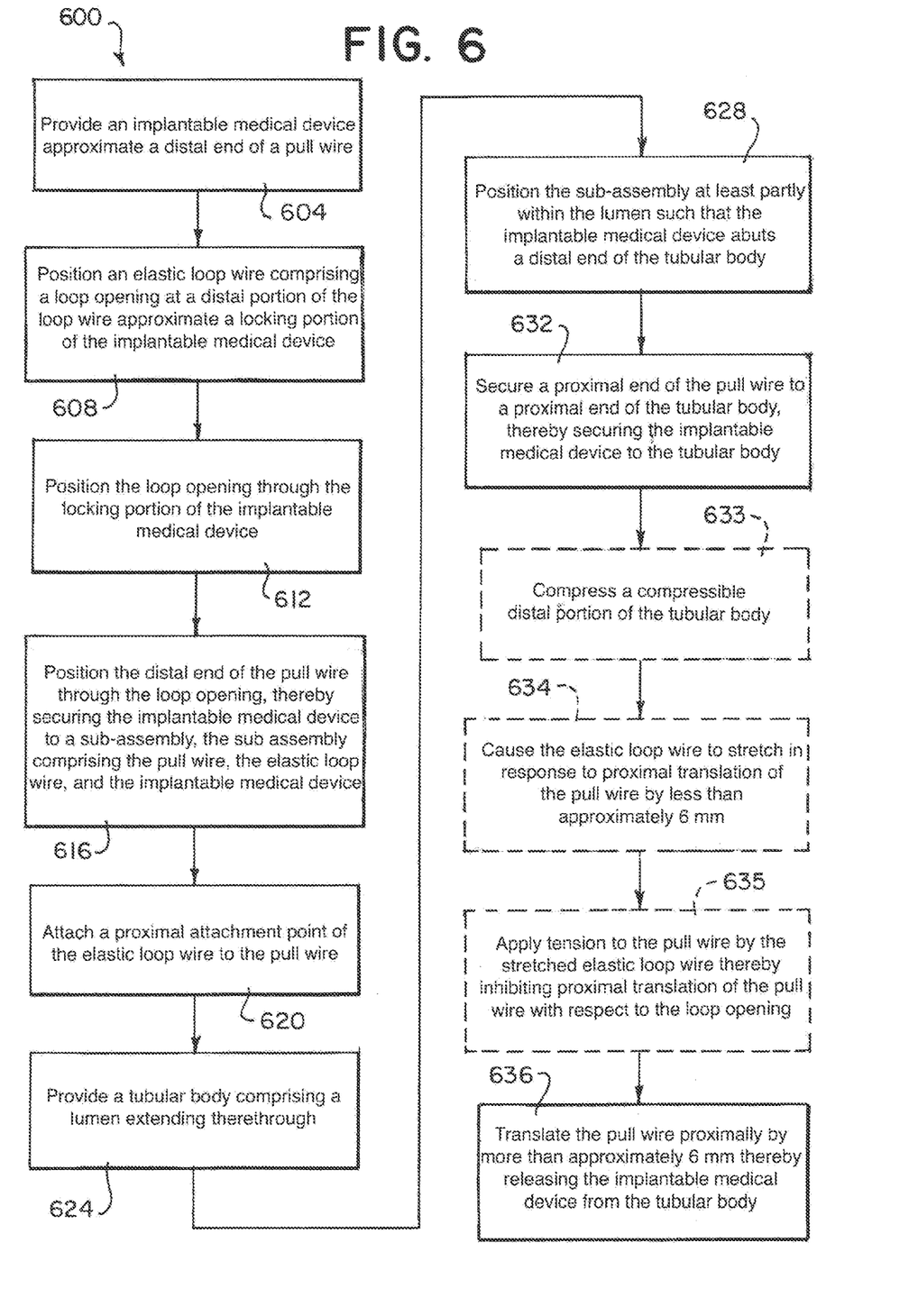
FIG. 6 is a flowchart of an example method of using the delivery member, according to aspects of the present invention.

FIG. 6 is a flowchart of an example method of using the delivery system, according to aspects of the present invention. In block 604, the method can include providing an implantable medical device 12 approximate a distal end 144 of a pull wire 140. In block 608, the method can include positioning a loop opening 405 of an elastic loop wire 400 approximate a locking portion 18 of the implantable medical device 12. The loop opening 405 can be located at a distal portion of elastic loop wire 400. In block 612, the loop opening 405 can be positioned through the locking portion 18 of the implantable medical device 12. In block 616, the distal end 144 of the pull wire 140 can be positioned through the loop opening 405. The distal end 144 of the pull wire 140 can thereby secure the implantable medical device to the elastic loop wire 400 and pull wire 140, to form sub-assembly 450. The sub-assembly 450 can include the implantable medical device 12, the elastic loop wire 400, and the pull wire 140.

In block 620, a proximal attachment point 410 of elastic loop wire 400 can be attached to the pull wire 140. Now the loop opening 405 located on distal end 404 of loop wire 400 is secured to the distal end 144 of the pull wire 140 and the loop wire 400 is secured to the pull wire 140 at the proximal attachment point 410 at a location proximal to the distal end 404 of loop wire 400.

In block 624, the method can include providing a tubular body 90. The tubular body can include a lumen 608 extending therethrough. As discussed in reference to FIG. 1, the tubular body can include proximal tube 100, support coil 550, distal tube 570, support tube 110, and inner support tube 510.

In block 628, the method can include positioning the sub-assembly 450 at least partly within the lumen 608 such that the implantable medical device abuts a distal end 94 of the tubular body 90. For example, a proximal end of the sub-assembly 450 can be inserted through the distal end 94 of the tubular body 90 until the implantable medical device 12 abuts the distal end 94 of tubular body 90.

In block 632, a proximal end of the pull wire 140 can be secured to a proximal end 92 of the tubular body 90, thereby securing the implantable medical device 12 to the tubular body 90. For example, a proximal end of pull wire 140 can be positioned through support tube 110, and a pull wire bead 142 can be welded, glued, or otherwise attached to the proximal end of the pull wire after it has been positioned through proximal support tube 110 of the tubular body 90. The pull wire bead 142 can be sized such that the pull wire bead 142 is larger than the space (lumen) between the proximal support tube 110 such that the pull wire bead 142 interferes with the proximal support tube 110 and proximal support tube 110 retains the pull wire bead 142 proximal to the proximal tube 100.

In optional block 633, the method can include compressing a compressible distal portion 300 of the tubular body 90. For example, before proximal end of the pull wire 140 is secured to a proximal end 92 of the tubular body, the pull wire 140 can be tensioned to a predetermined tension, thereby preloading or pre-tensioning the pull wire causing the compressible distal portion 300 to be compressed.

In optional block 634, the method can include causing the loop wire to stretch in response to proximal translation of the pull wire by less than approximately 6 millimeters. In optional block 635, the method can include applying tension to the pull wire 140 by the stretched elastic loop wire 400 to thereby inhibit proximal translation of the pull wire 140 with respect to the loop opening 405. Accordingly, the tensioned loop wire 400 can be effective to prevent premature detachment of the implant 12 from the delivery system 10.

In block 636, the method can include translating the pull wire proximally by more than approximately 6 millimeters to thereby release the implantable medical device 12 from the tubular body 90 of delivery system 10.

According to some embodiments, the tubular body 90 can further include a proximal tube 100, a support coil 550 distal to proximal tube 100, and a distal tube 570 distal to the support coil 550.

In some embodiments, attaching the proximal attachment point 410 of the elastic loop wire 400 to the pull wire can include tying one or more knots between respective ends 406, 408 of the loop wire 400 to the pull wire. In some embodiments, attaching the proximal attachment point 410 of elastic loop wire 400 to the pull wire 140 can include welding respective ends 406, 408 of the elastic loop wire 400 to the pull wire 140.

According to some embodiments, the distal tube 570 can include a compressible distal portion 300. The method can include compressing the compressible distal portion 300, translating the pull wire proximally by more than approximately 6 millimeters and decompressing the compressible distal portion 300 thereby providing an elastic force E against the implantable medical device 12 that facilitates the release of the implantable medical device 12 from the tubular body 90.

The descriptions contained herein are examples of embodiments of the invention and are not intended in any way to limit the scope of the invention. As described herein, the invention contemplates many variations and modifications of the implantation system and associated methods, including alternative geometries of system components, alternative materials, additional or alternative method steps, etc. Modifications apparent to those skilled in the pertinent art are intended to be within the scope of the claims which follow.

The invention claimed is:

1. A delivery system for deploying an implantable medical device to a target location of a body vessel, the delivery system comprising:
 a tubular body comprising a lumen extending therethrough;
 a pull wire extending through the lumen, the pull wire comprising a distal portion; and
 an elastic loop wire comprising a loop opening at a distal portion of the elastic loop wire positioned approximate a distal end of the tubular body and a proximal attachment point affixed to the pull wire, the elastic loop wire forming a fully closed loop,
 wherein the pull wire extends through the fully closed loop and contacts the elastic loop wire at both the proximal attachment point and the loop opening at a distal portion of the elastic loop wire,
 wherein the elastic loop wire and the pull wire are positioned to secure the implantable medical device to the delivery system,
 wherein the elastic loop wire is effective to inhibit premature detachment of the implantable medical device from the delivery system by inhibiting proximal translation of the pull wire with respect to the loop opening of the elastic loop wire.

2. The delivery system of claim 1, the tubular body further comprising:
 a proximal tube;
 a support coil distal to the proximal tube; and
 a distal tube distal to the support coil.

3. The delivery system of claim 1, wherein the pull wire is translated proximally by more than approximately 6 mm, thereby releasing the implantable medical device from the delivery system.

4. The delivery system of claim 3, wherein the elastic loop wire is configured to stretch lengthwise in response to the proximal translation of the pull wire.

5. The delivery system of claim 4, wherein the stretching of the elastic loop wire applies tension to the pull wire that inhibits proximal translation of the pull wire with respect to the loop opening of the elastic loop wire.

6. The delivery system of claim 2, wherein the support coil comprises interference cuts.

7. The delivery system of claim 2, wherein:
 the distal tube further comprises a compressed distal portion positioned approximate the implantable medical device; and
 the compressed distal portion provides an elastic force against the implantable medical device thereby facilitating release of the implantable medical device from the delivery system.

8. The delivery system of claim 7, wherein the compressed distal portion further comprises a spiral cut portion of the distal tube.

9. The delivery system of claim 1, wherein the elastic loop wire has a Young's Modulus of approximately 2 GPa.

10. The delivery system of claim 1, wherein the proximal attachment point of the elastic loop wire comprises a weld to the pull wire.

11. The delivery system of claim 1, wherein the proximal attachment point of the elastic loop wire comprises one or more knots between respective ends of the elastic loop wire and the pull wire.

12. The delivery system of claim 1, wherein the pull wire comprises a nonelastic material.

13. The delivery system of claim 2, wherein the distal tube further comprises interference cuts in the tubular body.

14. A delivery system for deploying an implantable medical device to a target location of a body vessel, the delivery system comprising:
 a tubular body comprising a lumen extending therethrough;
 a pull wire extending through the lumen, the pull wire comprising a distal portion; and
 an elastic loop wire comprising a loop opening at a distal portion of the elastic loop wire positioned approximate a distal end of the tubular body and a proximal attachment point affixed to the pull wire,
 wherein the elastic loop wire is configured to stretch lengthwise in response to proximal translation of the pull wire,
 wherein the elastic loop wire is effective to inhibit premature detachment of the implantable medical device from the delivery system by inhibiting proximal translation of the pull wire with respect to the loop opening of the elastic loop wire, and
 wherein the pull wire slides along the loop opening during proximal translation of the pull wire.

15. The delivery system of claim 14, the tubular body further comprising:
 a proximal tube;
 a support coil distal to the proximal tube; and
 a distal tube distal to the support coil.

16. The delivery system of claim 15, wherein the support coil comprises interference cuts.

17. The delivery system of claim 15, wherein:
 the distal tube further comprises a compressed distal portion positioned approximate the implantable medical device; and the compressed distal portion provides an elastic force against the implantable medical device thereby facilitating release of the implantable medical device from the delivery system.

18. The delivery system of claim 17, wherein the compressed distal portion further comprises a spiral cut portion of the distal tube.

19. The delivery system of claim 14, wherein the proximal attachment point of the elastic loop wire comprises a weld to the pull wire.

20. The delivery system of claim 14, wherein the stretching of the elastic loop wire applies tension to the pull wire that inhibits proximal translation of the pull wire with respect to the loop opening of the elastic loop wire.

* * * * *